(12) United States Patent
Frudakis (10) Patent No.: US 7,593,816 B2
(45) Date of Patent: Sep. 22, 2009

(54) METHODS AND APPARATUS FOR USE IN GENETICS CLASSIFICATION INCLUDING CLASSIFICATION TREE ANALYSIS

(75) Inventor: Tony Nick Frudakis, Sarasota, FL (US)

(73) Assignee: DNAPrint Genomics, Inc., Sarasota, FL (US)

( * ) Notice: Subject to any disclaimer, the term of this patent is extended or adjusted under 35 U.S.C. 154(b) by 698 days.

(21) Appl. No.: 10/496,226

(22) PCT Filed: Dec. 2, 2002

(86) PCT No.: PCT/US02/38309

§ 371 (c)(1),
(2), (4) Date: May 19, 2004

(87) PCT Pub. No.: WO03/048999

PCT Pub. Date: Jun. 12, 2003

(65) Prior Publication Data

US 2007/0042362 A1    Feb. 22, 2007

Related U.S. Application Data (60) Provisional application No. 60/338,734, filed on Dec. 3, 2001.

(51) Int. Cl.
*G06F 19/00* (2006.01)
(52) U.S. Cl. ...................................................... 702/19
(58) Field of Classification Search ....................... None
See application file for complete search history.

(56) References Cited

U.S. PATENT DOCUMENTS 5,541,067 A    7/1996  Perlin
6,291,182 B1   9/2001  Schork et al.

OTHER PUBLICATIONS

Nelson et al. A Combinatorial Partitioning Method to Identify Multilocus Genotypic Partitions That Predict Quantitative Trait Variation. Genome Research vol. 11, pp. 458-470 (2001).*
Jansen et al. High Resolution of Quantitative Traits Into Multiple Loci via Interval Mapping Genetics vol. 136, pp. 1447-1455 (1994).*
Bhadra et al. Interactins Among Dosage-Dependent Trans-Acting Modifiers of Gene Expression and Position-Effect Variegation in Drosophila Genetics vol. 150, pp. 251-263 (1998).*
Lee et al. Genetics of hypertension: from experimental models to clinical applications Journal of Human Hypertension vol. 14, pp. 631-647 (2000).*
Cordell Epistasis: what it means, what it doesn't mean, and statistical methods to detect it in humans Human Moleculat Genetics vol. 11 pp. 2463-2468 (2002).*
Weintrob N et al, Type 1 diabetes environmental factors and correspondence analysis of HLA class II genes in the Yemenite Jewish Community in Israel, Diabetes Care 2001 United States, vol. 24, No. 4, Apr. 2001, pp. 650-653.
Mayer S, et al., "Haplotype Study of the HLA-A,B,C and Bf Associations by the Factorial Correspondence Analysis", Journal of Immungenetics, vol. 8, No. 1, 1981, pp. 7-14.
M.J. Greenacre, L. Degos: "Correspondence Analysis of HLA Gene Frequency Data from 124 Population Samples", American Society of Human Genetics, 1977, pp. 60-75.
Lucek Paul et al., "Multi-locus nonparametric linkage analysis of complex trait loci with neural networks", Human Heredity, vol. 48, No. 5, Sep. 1998, pp. 275-284.
Fellenberg Kurt et al, "Correspondence analysis applied to microarray data", Proceedings of the National Academy of Sciences of the United States, vol. 98, No. 19, Sep. 11, 2001, pp. 10781-10786.
Tertwilliger J D et al, "Gene mapping in the 20th and 21st centuries: statistical methods, data analysis and experimental design" Human Biology, XX XX, vol. 72, No. 1, Bebruary 2000 (200-02), pp. 63-132.
Lander and Kruglyak, "Genetic Dissection of Complex Traits: Guidelines For Interpreting and Reporting Linkage Results", Nature Genetics, New York, NY, US, vol. 11, Nov. 1995, pp. 241-247.
J.S. Palmer et al., "Melanocortin-1 Receptor Polymorphisms and Risk of Melanoma: Is the Association Explained Solely by Pigmentation Phenotype?", AM> J. Hum. Genet., vol. 66, 2000, pp. 176-186.
EP Search Report for Application No. 02789948.3, Date, Jul. 3, 2006.
Cheverud, James M., "Detecing Epistasis Among Quantitative Trait Loci", Epistasis and Evolutionary, Date Jul. 20, 2000, pp. 58-69, Oxford University Press, USA.

* cited by examiner

*Primary Examiner*—John S Brusca
(74) *Attorney, Agent, or Firm*—John J. Oskorep, Esq.

(57) ABSTRACT

Methods and apparatus for use in genetic trait classification involving at least two genes associated with a genetic trait are described. In one illustrative method, a value for use in classifying an individual into one of a plurality of trait classes associated with the genetic trait is calculated. The value is calculated based on (1) a sum of contributions associated with each genotype of a plurality of genotypes of the at least two genes identified for the individual, where the contributions for each genotype are identified at least in part from statistical associations between the genotypes and each trait class identified in a sample population; and (2) a sum of contributions associated with each one of one or more genotype combinations between the at least two genes identified in the individual, where the contributions for the one or more genotype combinations are identified at least in part from statistical associations between the genotype combinations and each trait class identified in the sample population. Advantageously, epistasis as well as additivity and dominance affects are taken into account for more accurate genetic trait classifications.

17 Claims, 3 Drawing Sheets

METHODS AND APPARATUS FOR USE IN GENETICS CLASSIFICATION INCLUDING CLASSIFICATION TREE ANALYSIS

CROSS REFERENCE TO RELATED APPLICATIONS

This application is a national phase filing under 35 U.S.C Sect. 371 of PCT International Application Number PCT/US 02/38309 having an International Filing Date of Dec. 2, 2002, claiming earlier priority to U.S. Provisional Patent Application No. 60/338,734 having a filing date of Dec. 3, 2001, both of which are hereby incorporated by reference herein.

TECHNICAL FIELD

The present invention relates to genetic classification and more particularly to blind genetics classification using complex genetics techniques.

BACKGROUND INFORMATION

The purpose of genetics classification is to be able to accurately classify individuals into one of a plurality of genetic trait classes (e.g. brown, blue, green, etc.) associated with a particular genetic trait (e.g. eye color). A genetics classification test should be able to identify with precision which trait class an individual may fall into based on a genetic sample taken from the individual. The present application relates to the use of complex genetics analysis and software to create or construct accurate genetics classification tests. Such classification tests have highly valuable applications, especially in the fields of personalized medicine and criminal investigation.

The present application relates more particularly to "blind" genetics classification. "Blind genetics classification" is the classification of individual genetic samples that were not used in constructing the actual classification tool. If 1000 samples were being considered, for example, a classification model may be built from 900 of them. Classification of the 900 individuals will perform at one level (depending on the genes used), and blind classification of the remaining 100 should perform as well. However, the blind classification may not perform well at all, depending on how well the classification model generalizes.

The problem with many of the existing classification methods used in genetics or genomics analysis is that they build good models, but the models tend not to generalize very well. That is to say, the models produced are "over-fit" to the data. This is not surprising when one recognizes that these methods were not developed with the specific requirements of complex genetics analysis in mind. Linear discriminate methods and Bayesian probability models, for example, overestimate the importance of single genotype associations, which means they are sensitive to dominance and even additive issues but they ignore higher-order interactions that are referred to in genetics as non-linear/interactions or epistasis. Upon blind challenge, they therefore under perform using the same set of data when compared to the present inventive techniques described herein.

Some methods measure complex genetics parameters (the so-called "parametric" methods) and, for this reason, are encumbered with many limitations. Some of these define the additive, dominance, and interactive contribution of gene variants based on trait value. To measure these values, the programs use regression analysis. These methods build models that appear to be highly accurate when tested against samples that went into construction of the model but, for unclear reasons, they do not tend to generalize as well for blind classification than the present methods described herein, perhaps because parameter estimation is particularly sensitive to inadequate sample sizes.

Assume that the trait of skin color is a function of two genes A and B, and each gene has various forms (i.e. haplotypes) in the population A1, A2, . . . , to An, and B1, B2, . . . , to Bn. It may be that A1 always specifies dark skin, but A2 specifies dark skin when paired with B1 and light skin when paired with B2. In this case, the influence of A1 is said to be dominant and the influence of A2 is said to be interactive. Each human being has two copies of every gene. One person may have A1/A1 and B1/B1, whereas another person may have A1/A2 and B1/B3. If an individual has no copies of A3, the skin color may be darker than average; if the individual has one copy of A3, the skin color may always be medium; and if the individual has two copies of A3, the skin color may be very light. In this case, A3 is said to have an additive effect on skin color.

Even though the genes that determine a trait may be known with confidence, using them to make accurate classifications for the trait is another matter all together. By analogy, just because one has a complete set of puzzle pieces, it is not immediately clear how they should be put together to constitute an image. Most human traits are a function of additive, dominance, and interactive influences amongst several genes, and breaking the impact of genes on traits into these three influences helps geneticists understand how traits are determined by specific gene variants and combinations of gene variants. Understanding how each form of each gene participates in the determination of a trait is a fundamental goal for genetics researchers.

Knowing this, it is possible to classify an individual into trait classes. In the fields of variable drug response, or disease predisposition, such ability has enormous social and economic implications. Various methods for using gene sequences to predict traits have been previously developed, including linear discriminate analysis and Bayesian classifications. Unfortunately, these methods do little to address the subtleties of gene-by-gene influences, or fully capture the impact of individual genotypes.

Consider an example which describes why it is difficult to make genetics classifications even though the genes impacting the trait are known with confidence. In this example, two genes A and B are specified. Assume the following sample "counts" for 658 people relative to skin shade.

TABLE A

Gene A genotypes and skin shades in Caucasians.

|       | Dark | Medium | Light |
|-------|------|--------|-------|
| A1/A1 | 101  | 4      | 3     |
| A1/A2 | 50   | 5      | 2     |
| A1/A3 | 10   | 23     | 22    |
| A2/A2 | 102  | 101    | 59    |
| A2/A3 | 20   | 31     | 20    |
| A3/A3 | 2    | 45     | 58    |

It can be determined from this data that people with the A1 genotype usually have Dark skin, but sometimes Medium or Light, and people with A2 usually do not have Light skin. Making classifications based on this knowledge results in the misclassification of only 28 A1 individuals, but 81 A3 individuals. In this case, it is better to make classification rules based on genotypes, such as A1/A1 being not light (correct 105/108 times), A1/A2 not being light (correct 55/57 times) etc.

Now consider a B gene with the following counts:

TABLE B

Gene B genotypes and skin shades in Caucasians.

| | Dark | Medium | Light |
|---|---|---|---|
| B1/B1 | 51 | 24 | 33 |
| B1/B2 | 50 | 10 | 2 |
| B1/B3 | 30 | 13 | 12 |
| B2/B2 | 52 | 141 | 69 |
| B2/B3 | 10 | 36 | 25 |
| B3/B3 | 12 | 25 | 68 |

A consideration of such B gene variants along with A variants may enable better classification. In this case, those with a B1 tend to have Dark color and those with B3 average a Lighter color, but do the 10 B2/B2 individuals with Dark color have a particular gene A genotype that distinguishes them from other B2/B2 individuals? For real genetics problems, it is rarely the case that those that were misclassified using gene A are correctly classified using gene B—oftentimes up to 10 more genes are required to explain all of the variability in the data, which is one example of why it is difficult to make genetics classifications even though the genes impacting the trait are known with confidence.

It has been observed that often the specific combination of A and B alleles that helps make accurate classifications. However, the way these combinations relate to trait value can be unpredictable. For this reason, observation is crucial for good genetics classification, and it is upon observation that the present inventive techniques described herein rely. For example, assume that the combinations of A and B gene variants provides a table with the following counts (shown in part):

TABLE C

Genotype combinations.

| | Dark | Medium | Light |
|---|---|---|---|
| A1/A1 + B1/B2 | 50 | 2 | 0 |
| A1/A3 + B1/B2 | 0 | 10 | 0 |
| Etc. | ... | ... | ... |

From Table C, it would appear that the A1/A1+B1/B2 combination is always predictive for "not Light" and usually predictive for Dark, and the A1/A3+B1/B2 combination is always predictive for "Medium" color. One of these results is not surprising, but the other is. From Table A and B, we see that both A1/A1 and B1/B2 are linked with Dark color on their own, so it is no surprise that people with the combination A1/A1+B1/B2 almost always have Dark color. In contrast, A1/A3 appears to be linked with no color on its own, and B1/B2 linked with Dark but the A1/A3+B2/B2 combination is linked with Medium color. In this case, the presence of the A1/A3 combination explains why some of the B1/B2 individuals in Table B are not Dark and the rule "the presence of B1/B2 indicates Dark unless A1/A3 is present" would have a higher blind classification accuracy than the rule "B1/B2 indicates Dark".

When a variant pair associated with one type of extreme trait is paired with another gene variant pair linked with the same extreme trait, an intermediate trait may sometime result. Sometimes it is two variants that are not linked to the trait at all on their own that together determine a specific trait value. The interaction between gene variants to influence trait value is called epistasis. These types of unexpected results are not unusual in genetics. Other data has suggested that this type of scenario is not at all uncommon, which illustrates that the present inventive techniques described herein are an important advance.

If A's influence and B's influence are known, then how is it that the influence of A+B cannot always be predicted prior to observation? In other words, how is it possible for epistasis to exist? Most dynamic biochemical pathways and their influences are complex. The product of each gene is part of myriad complex biochemical networks, and modification of a gene product in a dynamic biochemical pathway may have a small or large effect on the function of the pathway, depending on the position of the gene in the pathway and the type of modification. Many biochemical networks intersect with others, adding to the complexity and unpredictability that modifications in one pathway can produce. Most geneticists agree that linking a gene variant to a trait depends on observation rather than conjecture or inference from biochemical research. In other words, genetics observations do not always conform to expectations, not because the observations are not accurate but because genetics is very complex. It is very advantageous to learn how these modifications and variants participate in trait formation through observation. The present inventive techniques described herein is a tool for such observation.

With most human traits, certain variant combinations (called genotypes, such as A1/A1 or A1/A3) may be highly predictive for a trait, but other combinations not predictive. Certain variants (such as A1 or A3) may be predictive on their own, to varying extents specific to the variant, while others may not be. Certain combinations of variant combinations (genotypes) may be linked to a trait. However, each of the genotypes may not be linked to the trait, or linked in ways that are expected based on the combination linkage, or linked to in ways one would not expect based on the combination linkage. These are the complex issues that population geneticists must contend with when attempting to make practical applications of their research.

SUMMARY

What has been developed is a new technique for genetics classification that captures all three main components of genetic variance (additivity, dominance, and interaction) in an efficient computational manner. The present classification technique substantially outperforms existing techniques, and has been successfully applied to the classification of human iris colors from pigment gene haplotypes, as an example. The present technique uses a statistical significance for a gene variant, along with the combinations within which the variant are found in a study sample, in order to predict a genetic trait. The technique has outperformed other methods including straight linear or quadratic classification, neural networks, direction setting rules, Bayesian estimates, and classifications generated from standard quantitative genetics parameter estimates.

The methods and apparatus for use in genetic trait classification involve at least two genes associated with a genetic trait. In one illustrative method, a value for use in classifying an individual into one of a plurality of trait classes associated with the genetic trait is calculated. The value is calculated based on (1) a sum of contributions associated with each genotype of a plurality of genotypes of the at least two genes identified for the individual, where the contributions for each genotype are identified at least in part from statistical associations between the genotypes and each trait class identified from a sample population; and (2) a sum of contributions associated with one or more genotype combinations between the at least two genes identified for the individual, where the contributions for the one or more genotype combinations are identified at least in part from statistical associations between the genotype combinations and each trait class identified from the sample population.

Advantageously, epistasis as well as additivity and dominance affects are taken into account for more accurate genetic trait classifications. A useful classification tree analysis is also described.

MODES FOR CARRYING OUT THE INVENTION

The present technique may be viewed as a p-value method, a classification method constituting a blend of classification tree and linear discriminate classification using haplotype combinations. The present technique relates to producing a list of genotype combinations (SNPs or haplotypes, for example) and using the combinations that are of relatively pure trait value, along with the genotypes themselves, to make blind genetics classifications.

Methods for identifying the forms of a gene that are predictive of a trait have been developed (see, for example, U.S. patent application Ser. No. 10/120,804 entitled "Methods For The Identification Of Genetic Features For Complex Genetics Cassifiers"), which is an important first step. The present method advantageously incorporates measurements of predictive capability in terms of individual variants and variant combinations. In so doing, the method constructs classification rules that are sensitive to the three main forces that shape the influence of genes on traits—additive, dominance, and epistasis.

Consider the following genotype combinations, where the numbers represent specific variants (haplotypes or SNPs, as the case may be):

TABLE D

Hypothetical Genotypes for 4 genes and Skin Shade in Caucasians.

| | Gene 1 | Gene 2 | Gene 3 | Gene 4 | Color |
|---|---|---|---|---|---|
| DNAP0001 | 1, 1 | 1, 2 | 3, 4 | 1, 2 | Light |
| DNAP0002 | 1, 2 | 1, 1 | 2, 4 | 1, 1 | Dark |
| DNAP0003 | 1, 1 | 2, 2 | 2, 4 | 1, 1 | Dark |
| DNAP0004 | 1, 1 | 2, 2 | 2, 4 | 1, 4 | Medium |
| DNAP0005 | 1, 1 | 2, 2 | 1, 1 | 1, 1 | Medium |
| ... | ... | ... | ... | ... | ... |

Considering the additivity effects in connection with the above data, it may be that the Gene 3 genotype (2, 4) is linked with Medium color and the Gene 4 genotype (1, 1) is also linked with Medium color, but when they are found together they are strongly linked with Dark color. The two genotypes appear to contribute towards the production of some compound that begets Darker than average color, and when combined, the level of this compound becomes so great the result is Dark color. Considering the dominance effects, it may be that the (1, 1) genotype of Gene 1 is always found in Light individuals and that if a person has the Gene 1 (1, 1) genotype, they will always have Light color regardless of the other genotypes for other genes present in the individual. The (1, 1) Gene 1 product may represent some sort of bottleneck in the pigmentation pathway, keeping the levels of pigment from accumulating. By analogy, this gene may represent a broken hose that keeps a car from running properly.

Considering the epistasis effects in connection with the above data, if Gene 3 (2, 4) and Gene 4 (1, 1) were not linked to either Light, Medium, or Dark, they would seem to be uninteresting. If when found together, however, Gene 3 (2, 4) and Gene 4 (1, 1) are always found in Dark individuals (see DNAP0002 and DNAP0003 in Table D), these two may interact epistatically to determine the trait. Existing conventional methods for genetics classification, such as linear discriminate procedures or Bayesian probability procedures, tend to be adept at capturing the additivity and especially the dominance components. However, these methods undesirably tend to be inept at capturing the epistatic component. In contrast, the present method considers all three of these elements when developing classffication rules.

Assume that Gene 1 (1, 1) and Gene 2 (1, 1) are the only allele combinations for any of these genes that are predictive of color on its own. Assume Gene 1 (1, 1) alleles are strongly associated with Light color (a chi-square statistic would have a low p-value for association with "light") and the Gene 2 (1, 1) genotype is associated with "Dark color." A value based on the following mathematical expression may be used to help classify an individual:

$$\Sigma n v_i \qquad (1)$$

for all genes i, where $v_i = \log(c/p_i)$ where c is suitably chosen constant greater than or equal to 0.05 and n is a convenient dummy variable for the different traits, say, n=+1 for Light or n=−1 for Dark. As apparent, the resulting value from expression (1) will be greater for sample DNAP0001 than sample DNAP0002 because the former has the (1, 1) genotype which is significantly associated with Light and the latter has the (1, 2) genotype which is significantly associated with Dark. Further, the stronger the association between Gene 1 (1, 1) and Light, the lower the p-value ($p_i$) and the greater the absolute value of the score $v_i$ (since the linkage is with Light the more positive it becomes; if it were linked with Dark, it would become more negative).

The following classification rule might be developed based on the results of this example: a positive value means the sample should be classified to Light, and a low value means the sample should be classified to Dark. Using this rule, the two samples can be classified into the proper group. With complex traits, however, it is almost never the case that a single gene causes a particular trait Gene 1 may exert a strong influence on the trait value, but its influence may be a function of the context within which it is found.

For example, if the Gene 2 (1, 2)+Gene 3 (3, 4) combination was always found in persons of Dark color such that the following profiles were obtained:

TABLE E

| Gene 1 | Gene 2 | Gene 3 | Dark | Medium | Light |
|--------|--------|--------|------|--------|-------|
| 1, 1   | 1, 1   | 3, 4   | 24   | 21     | 22    |
| 1, 1   | 1, 2   | 3, 4   | 46   | 0      | 0     | and the following counts for combinations were obtained.

TABLE F

Counts of observed genotype combinations in each color class, for each possible 2-gene pair (only parts of 2 such pairs shown).

|              | Dark | Medium | Light |
|--------------|------|--------|-------|
| Gene 2 + Gene 3 |   |        |       |
| 1, 1 3, 4    | 25   | 23     | 32    |
| 1, 1 1, 1    | 56   | 0      | 0     |
| 1, 1 1, 2    | 35   | 3      | 12    |
| 1, 2 3, 4    | 3    | 5      | 1     |
| 1, 2 1, 1    | 7    | 9      | 0     |
| ...          | ...  | ...    | ...   |
| Gene 3 + Gene 4 |   |        |       |
| 1, 1 2, 3    | 34   | 77     | 34    |
| ...          | ...  | ...    | ...   |
| ...          | ...  | ...    | ...   |

It can be seen that the Gene 2 (1, 1)+Gene 3 (1, 1) combination is only found in individuals with Dark color. A numerical score can be given to individuals possessing this Gene 2/Gene 3 combination that adjusts their total score towards Dark (e.g. −1 or −0.5 or some other value, perhaps based on the "purity" of trait value for the combination), and adds it to the other score derived from expression (1) to arrive at a more complete prediction.

Thus, scores should also be compiled for genotype combinations between the genes based on the expression $$\Sigma n c_j \quad (2)$$

for all "significant" genotype combinations j identified in the sample population, where $c_j$ is the indicator function of the jth genotype combination, that is $c_j=0$ or 1 (0 if the jth combination is not present in the individual or $c_j=1$ if it is present), and n is a convenient dummy variable for the different traits, say n=+1 or −1 (+1 for Light color trait or n=−1 for Dark color trait). "Significant" genotype combinations are those combinations in the sample population which are overwhelmingly or statistically of one particular trait class (e.g. Dark skin) or another (e.g. Light skin) (e.g. perhaps always, or 94% of the time, depending on the data set).

Thus, to formulate a more complete expression and/or calculate a final classification value:

$$\Sigma n v_i + \Sigma n c_j \quad (3)$$

for all genes i and all significant genotype combinations j.

In Table F above, it is required that a genotype combination be over 94% pure—that is, over 94% of the counts are of one color. This requirement makes the Gene 2 (1, 1)+Gene 3 (1, 1) combination the only combination of those shown that influences the classification score. If the list was, for example, a thousand pages long for thousands of possible combinations, and this combination was the only one that met this requirement, the score in each individual to be classified from expression (2) would be based only on this genotype combination. If there are no combinations that meet this requirement, even if there are thousands of pages of such combinations, the score from expression (2) would be zero for each individual to be classified. Alternatively, j may be a number of all possible genotype combinations amongst all of relevant genes and $c_j$ may be based on a p-value from the associations.

Advantageously, expression (2) allows for a consideration of observations indicative of epistasis when making classifications. Consider three (3) genes, where there are six (6) possible 2-gene combinations.

1,1
1,2
1,3
2,2
2,3
3,3

Each one of these genes has genotypes, and in a population of people, there will be a list of observed combinations, such as shown in the following Table G.

TABLE G

| Genes | Genotypes |      |
|-------|-----------|------|
| 1, 1  | 1, 1      | 1, 1 |
|       | 1, 2      | 1, 1 |
|       | 1, 3      | 1, 1 |
|       | 1, 1      | 1, 2 |
|       | 1, 2      | 1, 2 |
|       | 1, 3      | 1, 3 |
| 1, 2  | 1, 4      | 1, 1 |
|       | 1, 5      | 1, 1 |
|       | 1, 6      | 1, 1 |
|       | 1, 4      | 1, 2 |
|       | 1, 5      | 1, 2 |
|       | 1, 6      | 1, 3 |
| 1, 3  | 1, 7      | 1, 1 |
|       | 1, 8      | 1, 1 |
|       | 1, 9      | 1, 1 |
|       | 1, 7      | 1, 2 |
|       | 1, 8      | 1, 2 |
|       | 1, 9      | 1, 3 |
| 2, 2  | 2, 0      | 1, 1 |
|       | 2, 1      | 1, 1 |
|       | 2, 2      | 1, 1 |
|       | 2, 0      | 1, 2 |
|       | 2, 1      | 1, 2 |
|       | 2, 2      | 1, 3 |
| 2, 3  | 2, 3      | 1, 1 |
|       | 2, 4      | 1, 1 |
|       | 2, 5      | 1, 1 |
|       | 2, 3      | 1, 2 |
|       | 2, 4      | 1, 2 |
|       | 2, 5      | 1, 3 |
| 3, 3  | 2, 6      | 1, 1 |
|       | 2, 7      | 1, 1 |
|       | 2, 8      | 1, 1 |
|       | 2, 6      | 1, 2 |
|       | 2, 7      | 1, 2 |
|       | 2, 8      | 1, 3 |

Each of these observed combinations has a group of individuals that possess the combinations. If a list of the individuals that possess this combination and their color is made from the study sample, the list may appear as follows:

TABLE H

| Genes | Genotype | | Associated Traits in the Sample Population |
|---|---|---|---|
| 1, 2 | 2, 9 | 1, 1 | DNAP0001 (Dark), DNAP0005 (Light) |
| | 3, 0 | 1, 1 | DNAP00012 (Dark), DNAP00052 (Light), DNAP00031 (Dark), DNAP0005 (Light) |
| | 3, 1 | 1, 1 | DNAP00021 (Dark), DNAP00025 (Dark), DNAP00091 (Dark), DNAP00065 (Dark), DNAP00014 (Dark), DNAP00035 (Dark), DNAP00071 (Dark), DNAP00075 (Dark) |
| | 3, 2 | 1, 2 | DNAP00051 (Dark), DNAP00055 (Light), DNAP00043 (Dark), DNAP00066 (Light) |
| | 3, 3 | 1, 2 | DNAP00020 (Dark), DNAP00065 (Light), DNAP00098 (Dark), DNAP00096 (Light) |
| | 3, 4 | 1, 3 | DNAP000455 (Dark), DNAP000511 (Light), DNAP00011 (Dark), DNAP0005 (Light) |
| 1, 4 | 3, 5 | 1, 1 | DNAP00022 (Dark), DNAP00076 (Light) |
| | 3, 6 | 1, 1 | DNAP00011 (Dark), DNAP00033 (Light), DNAP00095 (Dark), DNAP0005 (Light) |
| | 3, 7 | 1, 1 | DNAP000488 (Dark), DNAP00095 (Light), DNAP000788 (Dark), DNAP0005239 (Light) DNAP00201 (Dark), DNAP00705 (Light), DNAP00501 (Dark), DNAP00605 (Light) |
| | 3, 8 | 1, 2 | DNAP00015 (Dark), DNAP000566 (Light), DNAP00801 (Dark, DNAP00045 (Light) |
| | 3, 9 | 1, 2 | DNAP07001 (Dark), DNAP00065(Light), DNAP05001 (Dark), DNAP06005(Light) |
| | 4, 0 | 1, 3 | DNAP06001 (Dark), DNAP07005 (Light), DNAP00901 (Dark), DNAP00705 (Light) | and etc. for the other gene combinations. Rather than list the samples by name and color, the counts for each combination may merely be listed (example given for a single gene):

TABLE H'

| Genes | Genotype | | Dark | Medium | Light |
|---|---|---|---|---|---|
| 1, 2 | 4, 1 | 1, 1 | 1 | | 1 |
| | 4, 2 | 1, 1 | 2 | | 2 |
| | 4, 3 | 1, 1 | 8 | | 0 |
| | 4, 4 | 1, 1 | 2 | | 2 |
| | 4, 5 | 1, 2 | 2 | | 2 |
| | 4, 6 | 1, 2 | 2 | | 2 |

In Table H', the genotypes for genes 1 and 2 shown do not appear in individuals of Medium color, and combination gene 1: 4,3 gene 2: 1, 1 appear in Dark individuals 8/8 times. If Gene 1 and Gene 2 interact to form a trait, but Gene 1 and Gene 4 do not genotypes for the former will not be independently distributed among colors as is the case in Table H' above, whereas those for the latter would be. A simple chi-square test could be used to make this determination, or a % of purity for one color could be used.

Advantageously, making classifications based on contributions from both expressions (1) and (2) allows for all three of the types of genetics influence. Consider the following sample:

TABLE I

| Sample | Gene 1 | Gene 2 | Gene 3 |
|---|---|---|---|
| DNAP0010 | 1, 1 | 1, 1 | 3, 4 |

Assume that (a) Gene 1 allele 1 is linked with Dark but none of the alleles Gene 2, allele 1 and Gene 3, alleles 3 and 4 are linked with colors (b) the Gene 1 (1, 1) combination is strongly associated with Dark; and (c) none of these genotypes are found as part of combinations statistically linked to a particular color except the combination Gene 2 (1, 1)/Gene 3 (3, 4) which is weakly associated with Light color.

Based on the above, what is the best determination of color? The proper classification is likely "Dark" because of the strength of observations (a) and (b) relative to (c). In this case, either the additive or dominant influence of the 1 allele for Gene 1 overrides the interactive influence of the Gene 2/Gene 3 combination. Advantageously, the present technique captures the various contributions towards genetic trait determination and is capable of building a complex genetics model that performs well when challenged with blind samples.

To identify the proper classification, one has to measure the relative influence of the Gene 1 (1, 1) combination against that of the Gene2/Gene3 combination. The score derived from adding the value from expression (1) to that from expression (2) ensures this. In this case, the score from (1) is quite negative (e.g. −1.5) as the individual has a genotype strongly associated with Dark (it has a low p-value and the absolute value of $v_i$ is high. The score from expression (2) is only slightly positive (say 0.1). The combined value is still quite negative (−1.4).

Thus, samples are classified into the proper trait class by first calculating a score based on the p-value of individual genotype associations using expression (1), and then adding to it a score based on the number of genotype combinations the sample harbors using expression (2), where only those combinations that are possessed by others of only one trait class are considered.

If a sample has many Dark genotypes, expression (1) would offer the correct classification on its own. If a sample has many Dark genotypes and many genotype combinations that are present only in Dark individuals, expression (1) gives a score indicating a Dark classification and expression (2) reinforces the "Dark" character of the score. If a sample has many Dark genotypes, the expression (1) offers a score indicating a Dark classification; however if the sample has many genotype combinations found only in Light individuals, the score would be corrected to account for this observation using expression (2). The outcome is dependent on the relative strength of the p-values in expression (1) and the combinations used in expression (2). Some individuals with Dark genotypes may have Light genotype combinations, and vice versa, and the score may indicate a Dark or a Light score, or perhaps a Medium score.

For expression (2), a list of all observed genotype combinations for all possible gene combinations is first made with the trait associations. When working with several genes, this list is usually quite long. By making a list of all possible genotype combinations and providing expression (2), it is assured that those that influence trait value are properly considered when making classifications.

The value produced from adding the result of expressions (1) and (2) will produce a large set of numbers. If the proper genes and genotypes are used in the analysis, these values are usually excellent encodings for trait values. These encodings can be used to subsequently make classifications. The scores produced from a sum of those scores using expressions (1) and (2) can be used to make classifications, for example, by selecting threshold values (for example, −1.5 or more negative means "Dark"; between −1.5 and 0 means "Medium", and above 0 means "Light"). Alternatively, the values can be used as inputs for commonly available software packages, such as SAS or S plus software. Using SAS, for example, a linear discriminate method can be used to develop the most efficient use of the values when making classifications. Alternatively, a neural network, genetic algorithm or classification tree, for example, could be used. For that matter, a neural network, genetic algorithm, or classification tree could be used to define the best dummy variables for use with (1) and (2), as well as for deciding on how to use the value derived from the sum of (1) and (2) for classification.

To the values produced by expressions (1) and (2), one may apply some of the other methods that geneticists tend to use on their own, but providing superior results. Examples of such methods include linear discriminate methods or Bayesian probability methods. One may simply perform a cursory inspection of the results and notice that individuals with certain scores tend to be of a certain trait value, while others of a different value may be of another value, and thereby devise a very simple method for using the values to make classifications. For example, if all individuals with a value below −1.5 are "Dark", and if all individuals with a value above zero (0) are "Light", while those with a value between −1.5 and 0 are of mixed trait value, one might conclude that individuals below −1.5 are "Dark", those with a value above zero (0) are Light and every other trait value indicates an inconclusive classification—without using a neural network or genetic algorithm (this would be similar to a very simple classification tree).

The threshold values to be used when making blind classifications can be determined by applying other commonly used methods which most genetics researchers use on their own. Such methods include neural network methods, genetic algorithms, linear discriminate methods, or classification trees; each of these methods may be tried and the method that offers the best blind classification rate can be selected for use. Thus, the present method may be viewed as an empirical tool that strongly relies on observations from the data to make accurate classifications. For some problems, the values that signify one trait value are dearly distinct from those for another, and classification rules can be developed by eye. For other problems, one of the above methods must be applied to use the values to make accurate classifications.

The combination scores produced by expression (2) can be varied by using a neural net or genetic algorithm. For example, perhaps genotype combinations that are of only one trait value must be used to develop a model that performs optimally. We call these "pure" combinations. In some cases, combinations of 94% purity should be used to obtain the optimal results. Which combinations to use may be determined by applying a simple chi-square statistic. Those with p-values below 0.05 may be used for optimum results for some problems, while those with p-values below 0.01 may be needed for optimum results with another problem. All of the possibilities should be tried in order to make best use of the claimed method. For each problem, the "parameters" to be used will likely be unique and empirically determined. Each type of genetic classification problem is defined by its own set of genetic variants that interact in ways that are specific for the problem. For human eye color, 3- or 4-gene combinations may be the most informative, while for simple diseases like sickle cell anemia, combinations may not be needed at all. Again, the method may be advantageously used as part of an empirical process.

Sometimes, the use of 2-gene combinations enable the construction of a model that performs better upon blind challenge than a model using 3-gene or 4-gene combinations. The n of the n-locus combination that performs the best must again be determined empirically and, again, existing methods may allow for a rapid definition of n. One may test at least cases where n=2, 3, 4, and 5. Beyond n=5, and given the limitations on sample size that economic principles impose on genetics research, the sample sizes of each combination become too low for reliable use.

Linear and quadratic discriminate methods, and methods based on correspondence analysis, and others methods based on Bayesian probability analysis, Markov chain, and neural networks, have been previously described elsewhere. Applications of each of these methods produced models that usually perform well when one considers how well it classifies individuals that were used to construct the model (assuming appropriate input data are "features" of the problem). Blind classification, on the other hand, involves classifying individuals that did not go into construction of the model; it is a means by which to determine how well the model generalizes. Applied to the same data set, the method described herein outperformed these other methods in blind trials.

Thus, a value for use in classifying an individual into one of a plurality of trait classes associated with the genetic trait is calculated based on (1) a sum of contributions associated with each genotype of a plurality of genotypes of the at least two genes identified for the individual, where the contributions for each genotype are identified at least in part from statistical associations between the genotypes and each trait class identified from a sample population; and (2) a sum of contributions associated with one or more genotype combinations between the at least two genes identified for the individual, where the contributions for the one or more genotype combinations are identified at least in part from statistical associations between the genotype combinations and each trait class identified from the sample population.

As apparent, the present method applies to other suitable genetic traits as well, such patient response to a particular drug, or whether a patient has a particular disease or not, etc.

Human Iris Color and Pigmentation haplotypes as an Example. Linear discriminate and correspondence analysis methods have been previously used for analyzing pigmentation gene haplotypes to make classifications of individuals into proper eye color groups (see, for example, U.S. Provisional Application Ser. No. 60/377,164 entitled "Combined Correspondence Analysis And Linear/Quadratic Analysis For Constructing Complex Genetics Classifiers"; U.S. Provisional Application Ser. No. 60/338,524 entitled "A Correspondence Method For Constructing Complex Genetics Classifiers"; and U.S. Provisional Application Ser. No.

60/338,468 entitled "Linear And Quadratic Methods For Constructing Complex Genetics Classifiers". The above methods produced a useful model based on about 400 individuals, whereby blind classification of an additional 100 offered at least 94% accuracy. Subsequently, the sample size increased to 881. Using 781 of these to construct a model, and using prior methods, the blind classification accuracy dropped to 85%.

On the other hand, using the same exact data set with the present techniques described herein, when combined with a linear discriminate method, and using the values produced from expressions (1) and (2) to make classifications, a 97% accuracy was obtained. As apparent, the present technique is more sensitive to the very specific parameters that the analysis of genetics data require.

The present method was also used to obtain classification results with fewer associated genes. With other methods, it was required to use haplotype sequences from seven (7) different genes (OCA2, MYO5A, TYR, TYRP1, AIM, SILV, and DCT) on a sample size of 781 to obtain 85% blind classification accuracy on a sample size of 100. With the present method, a 94% accuracy on the same sample sizes using only the OCA2 and TYRP1 haplotypes were obtained. Using a linear discriminate method for employing the values derived from the sum of expressions (1) and (2) on OCA2 and TYRP1 haplotypes, the following classification results were obtained.

TABLE J

| Classification | Blue | Green | Hazel | Brown |
|---|---|---|---|---|
| Not Brown | 12 | 51 | 89 | 10 |
| Not Blue | 10 | 47 | 103 | 6 |

The accuracy of the "Not Brown" classification was 152/162=0.938. The accuracy of the "Not Blue" classification was 156/166=0.94. Total accuracy=94%.

Figure 1:
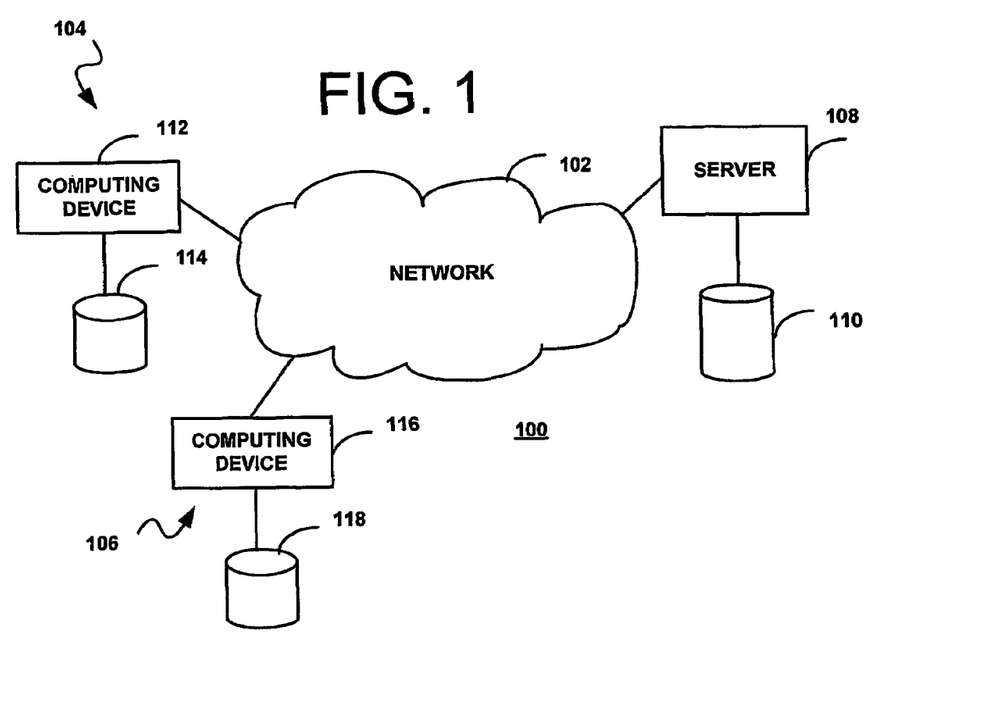
FIG. 1 is an illustration of a computer network having one or more computing devices for executing the methods described herein.

FIG. 1 is a block diagram of a computer system 100 which may execute the present techniques. Computer system 100 includes a network 102 and computer hosts 104 and 106. A server 108 and a database 110 which are coupled to network 102 are accessible by computer hosts 104 and 106. Each one of computer hosts 104 and 106 include one or more computing devices and databases. For example, computer network 104 includes a computing device 112 and a database 114, and computer network 106 includes a computing device 116 and a database 118. The computing devices may include any suitable computing device, such as a personal computer (PC) which has an input device (e.g. keyboard and mouse) and an output device (e.g. a visual display monitor). Any one of the databases, such as database 110, may hold or store the data for the sample populations (e.g. genotype data, and tables or lists of the statistical associations, etc.). The inventive software may be used in connection with and executed on, for example, computing device 112 of computer host 104. Although one computer system is shown and described in relation to FIG. 1, variations are not only possible, but numerous as one skilled in the art would readily understand.

Figure 2:
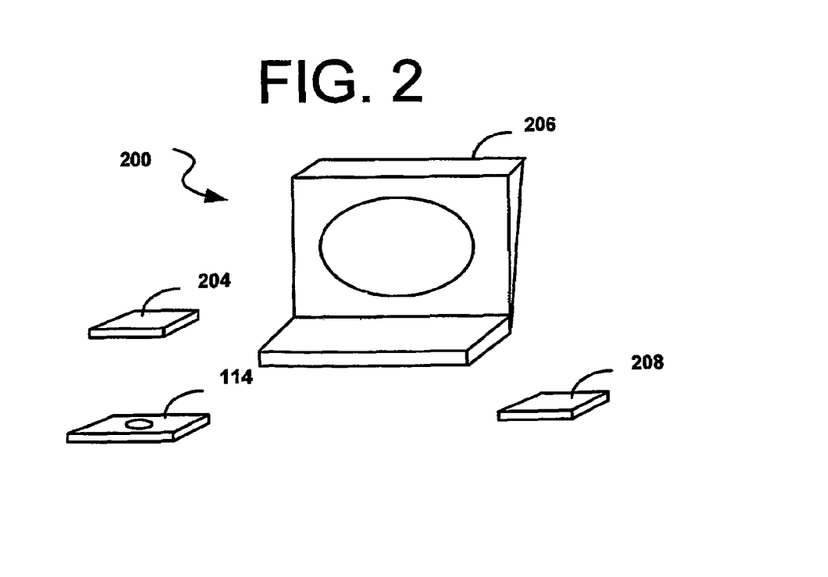
FIG. 2 is an illustration of various computer components which may be utilized for the methods described herein.

The methods described herein may be embodied and implemented in connection with FIG. 1 using software components 200 shown in FIG. 2. The software may be embedded in or stored on a disk 202 or memory 204, and executable within a computer 206 or a processor 208. Thus, the inventive features may exist in a computer storage medium which has computer instructions stored thereon, so that a computer processor can execute the instructions to perform the methods outlined in the computer instructions. Such software is preferably used in connection with and executed on computing device 112 of private network 104. Preferably, the system functions within the context of a PC network with a central Sun Enterprise server. The program can be loaded and run on any desktop PC that operates using the Linux or Unix operating system. Other versions could also function in a Windows environment. Alternatively, the software could operate on a publicly accessible server and available for use through a public network such as the Internet.

Figure 3:
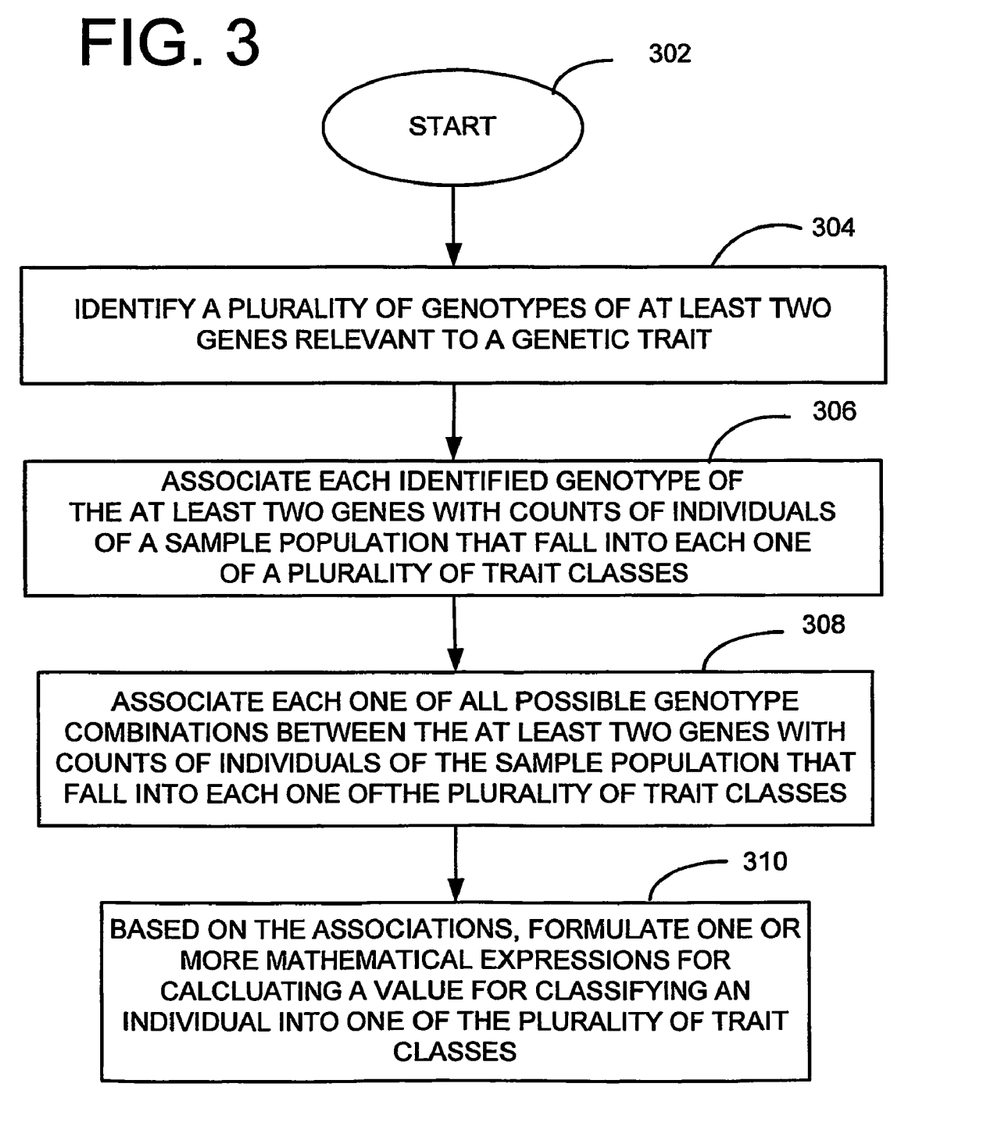
FIG. 3 is a flowchart which describes a method for use in classifying individuals into one of a plurality of trait classes for a particular genetic trait.

Referring now to the flowchart of FIG. 3, a method for use in genetic trait classification involving at least two genes is described. The method of FIG. 3 is a more abbreviated description of one approach taken based on the above. Beginning at a start block 302 of FIG. 3, a plurality of all possible genotypes of at least two genes relevant to a particular genetic trait are identified (step 304). This step 304 may be performed using any suitable conventional or non-conventional technique, including such techniques described in U.S. patent application Ser. No. 10/120,804 entitled "Methods For The Identification Of Genetic Features For Complex Genetics Classifiers". Once relevant genotypes are identified in the at least two genes, each genotype is associated with counts of individuals of a sample population that fall into each one of a plurality of trait classes for the particular genetic trait (step 306). For example, see Tables A and B in the Background section. Next, each one of all possible genotype combinations between the at least two genes are associated with count of individuals of the sample population that fall into each trait class (step 308). For example, see Tables H and H' above, which are abbreviated due to space considerations (this list could be a hundred or thousand pages long).

Based on the associations from step 306 and 308, one or more mathematical expressions are formulated for calculating a value for classifying an individual into one of the plurality of trait classes (step 310). For example, the above expressions (1) and (2), or expression (3), may be provided with the relevant data. As apparent, the mathematic expressions allow for contributions from individual genotypes present in the individual as well as contributions from genotype combinations present in the individual. As with expression (1) above, p-values for the associations may be calculated to help determine the contributions for each individual genotype. As with expression (2) above, each genotype combination may include only "significant" genotype combinations associated with a trait class having a count percentage in the sample population which exceeds a threshold.

Figure 4:
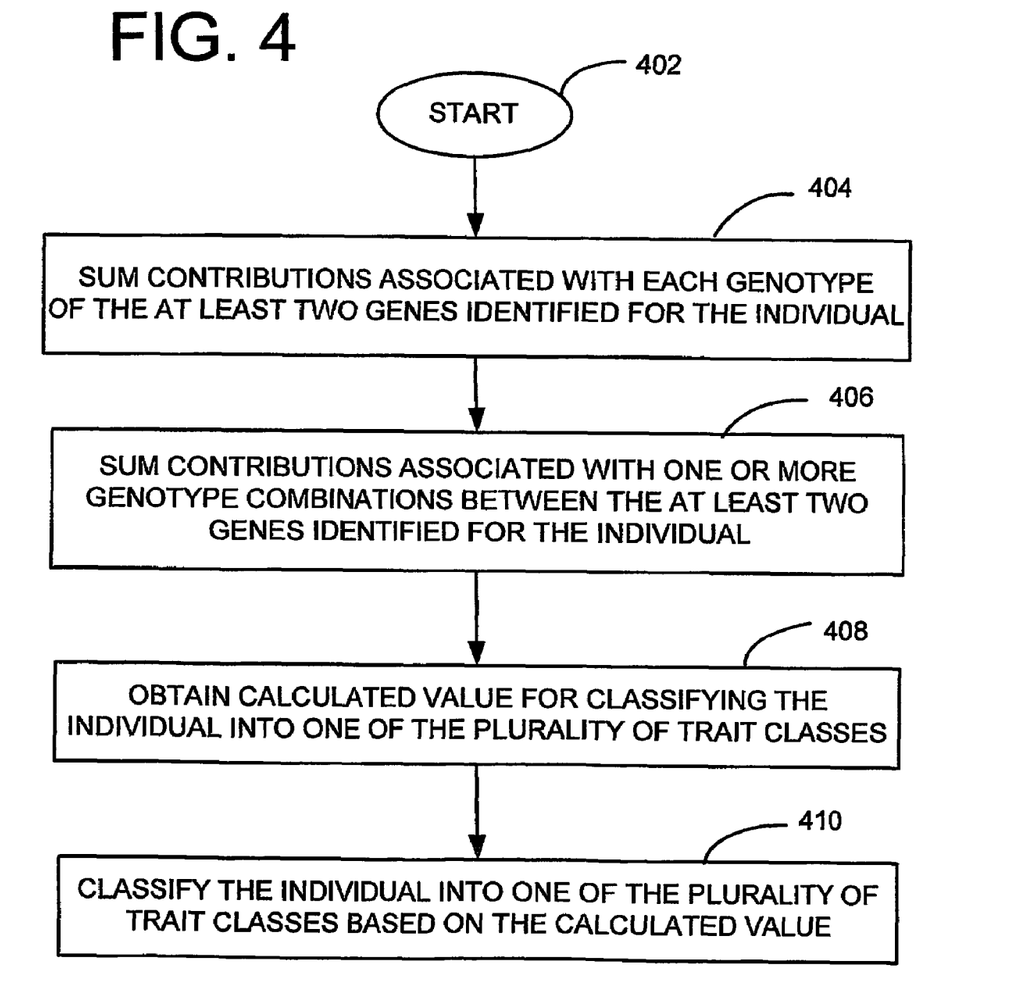
FIG. 4 is a flowchart which describes another method for use in classifying individuals into one of the plurality of trait classes for the genetic trait.

In the flowchart of FIG. 4, another method for use in genetic trait classification involving at least two genes is described. The method of FIG. 4 is another more abbreviated description of an approach taken based on the above, involving the execution of an expression for classifying an individual into one of a plurality of trait classes for a particular genetic trait. Beginning at a start block 402 of FIG. 4, contributions associated with each genotype of at least two genes identified for the individual are summed (step 404). In addition, contributions associated with each genotype combination between the at least two genes identified for the individual are summed (step 406). From these contributions, a calculated value for classifying the individual into one of the plurality of trait classes is obtained (step 408). For example, the contributions from step 404 and 406 may be added together. Based on the calculated value, the individual is accurately classified into one of the trait classes (step 410).

Classification Tree Analysis. The crux of this application is that genetics data, as considered in Tables F, H, and H', are crucial for accurate complex genetics classification. Functions (1) and (2) allow for their consideration in one convenient classification method. Another convenient classification method based on this type of table is based on Classification Tree analysis. What has also been developed is a nested statistical scheme by which to construct higher order genetic classification rules. The motivation for developing this scheme was a need to "solve" genetic associations in a manner that is respectful of complex genetics (i.e. epistasis and penetrance).

Classification trees have been previously used to solve a number of multivariate problems. However, most applications to date have focused on engineering and social problems. Though various classification tree methods have been used for protein and nucleic acid sequence phylogenetic and/ or ontological classification, it is believed that the approach has not yet been used in the field of complex (or other) human genetics as described herein. The present application claims priority to U.S. Provisional Patent Application Ser. No. 60/338,734 entitled "Classification Tree Methods For Constructing Complex Genetics Classifiers" filed on Dec. 3, 2001, which is hereby incorporated by reference herein.

The present scheme constructs a classification tree starting with a root, branching to nodes, and terminating in classification "leaves". A path along the tree represents a discrete compound genotype or compound genotype class. A compound genotype is an N-dimensional vector containing N diploid, phase-known genotype values (haplotype pairs). These genotype values are a subset of possible values for a haplotype system, which represent all observed phase-known haplotype pair values for a specific collection of polymorphic loci. An N-dimensional compound genotype vector is therefore a compound genotype with N genotype values from N different haplotype systems. A compound genotype class is a collection of compound genotype vectors incorporating compound genotype values from a common set of haplotype systems. A path from a root to a leave may lead to a compound genotype vector or a collection of compound genotype vectors that comprise a unique compound genotype class.

The present scheme builds a classification tree by defining the compound genotype vectors or compound genotype vector classes exhibiting the best statistical association with a particular trait value. The tree is built in a step-wise manner. A model (a growing path, or compound genotype class) is selected, terms (new haplotype systems) are added to the model, the new model is statistically tested, and either the new term is accepted or discarded. If it is accepted, either rules are formulated from its constituent compound genotypes or compound genotype classes (using chi-square statistics) and/or the model is expanded depending on the presence and strength of association between elements of the model and the trait value. The roots of the tree are genotypes of a randomly selected haplotype system. Nodes are randomly selected genotype classes, within which there are numerous different constituent genotypes. Edges connect X roots and N nodes to comprise X N+1 dimensional compound genotype classes.

The classification tree method may be useful for the classification of human eye colors. The tree is built by first selecting a set of roots and growing the edges to nodes based on the genetic distinction between individuals of light eye color shade (blue, green) and dark (black, brown) eye color shade within the new compound genotype class defined by the connection (hazel is always assigned to the eye color shade with the most members). For practical reasons, the distinction is only measured with respect to genotype value distributions within the last node. Within a compound genotype class, a pair-wise F statistic and associated p-value is used to measure the genetic structure differences between individuals of the various shade of eye colors, though it is possible to use an exact test p-value or a chi-square p-value with similar results. Individuals of ambiguous haplotype class (less than 75% certainty) are discarded and classified as "not classifiable".

All possible nodes not yet incorporated in the path from the root are tested during each new branching step, and the branch that results in the most distinctive partition (i.e. the lowest p-value) among the classes of eye color shade is selected. If there is no significant genetic structure within the new compound genotype class, the branching continues to another node (haplotype system), unless there are no more haplotype systems to consider or unless the sample size for the compound genotype class is below a certain pre-selected threshold (in which case a "no-decision" is specified). If the lowest p-value for the new compound genotype class is significant, rules are made from its constituent compound genotypes exhibiting significant chi-square residuals for association with a particular trait value. In this case, genotypes within the compound genotype class which are not explainable (for whom chi-square residuals are not significant, if any) are segregated from the rest of the compound genotypes within the compound genotype class to form new nested node(s), from which further branching is accomplished.

Nested nodes always represent new compound genotype classes at first. If branching from this nested node does not eventually result in the ability to create classification rules, the algorithm returns to the compound genotype class from which the nested node was derived and recreates Y nested nodes of Y constituent compound genotypes. In either case, nested nodes are only created from nodes with statistically significant population structure differences among the shade of eye color classes. For calculating the chi-square statistics leading to leaf formation, the algorithm first tries partitioning individuals along discrete trait value lines. If this is not significant, the algorithm condenses the discrete trait values into groups of like values (such as blue and green eyes versus brown and black eyes).

By restricting rule formation to constituents of compound genotype classes with significant genetic structure difference between groups of individuals with different trait values, in effect, this algorithm allows for the maximum amount of genetic variance contributed by the various combinations of haplotype systems to be learned. Once the tree has been completed, rules are produced from it by "reading" each path along the tree leading to a classification leaf, and these rules are used to predict the trait value of each individual. If the prediction rate is good (say 95% or greater) the process ends, and if it is not, the process is begun again starting with a new haplotype system for the root.

In the example applying the classification tree analysis to human eye color, five (5) haplotype systems (TYR2LOC920, OCA3LOC920, OCA3LOC109, TYRP3L105 and MCR3LOC105) were identified whose constituent haplotypes were predictive of human eye color. The classification tree method was applied to develop a tree from random combinations of TYR2LOC920, OCA3LOC920, OCA3LOC109, TYRP3L105 and MCR3LOC105 haploid genotype elements to form complex genetic classes associated with eye color shade (See Table K below).

TABLE K

Classification tree for using compound genotypes, or compound genotype classes, to categorize individuals as dark or light eye individuals. Similarity with the Tables F, H and H' can be seen, and the root for the claimed methods are based in the empirical observation of trait class counts for various genotypes and genotype combinations.

| | TYR2LOC920 | OCA3LOC920 | OCA3LOC109 | MCR3LOC105 | OCA3LOC109 | TYRP3L106 | CLASS | CORR | INCLASS | INCORR |
|---|---|---|---|---|---|---|---|---|---|---|
| 1. | AG/CA | CAC/CAC | | CCC/CYC | | GTT/GTT | DK/HAZ | 7 | 0 | 2 |
| 2. | AG/CA | CAC/CAC | | CCC/CYC | | GTT/TTT | LT/HAZ/B1 | 6 | 0 | 0 |
| 3. | AG/CA | CAC/CAC | | CCC/CYC | | GGA/GGT | INCONCL. | 0 | 4 | 0 |
| 4. | AG/CA | CAC/CAC | | CCC/CYC | | GGA/GTT | BLUE | 8 | 0 | 0 |
| 5. | AG/CA | CAC/CAC | | CCC/CYC | | GGA/GGA | DK | 2 | 0 | 0 |
| 6. | AG/CA | CAC/CAC | | CCC/CYC | | GGT/TGA | LT/HAZ | 4 | 0 | 0 |
| 7. | AG/CA | CAC/CAC | | NOT CCC/CYC | | | LT/HAZ | 14 | 0 | 1 |
| 8. | AG/CA | YGC/YRY | | CCC/CCY | | | LT/HAZ | 9 | 0 | 0 |
| 9. | AG/CA | YGC/YRY | | CCC/CTC | | | DK/HAZ | 3 | 0 | 0 |
| 10. | AG/CA | YGC/YRY | | OTHER | | | NOT OBS | 0 | 0 | 0 |
| 11. | AG/CA | TRC/CRC | | | | | INCONCL | 0 | 2 | 0 |
| 12. | AG/CA | OTHER | | | | | INCONCL | 0 | 1 | 0 |
| | | | | | | | TOTAL | 53 | 7 | 3 |
| 13. | AG/AG | | | CCC/CYC | ATA/ATR | GTT/KTT | DK/HAZ | 3 | 0 | 0 |
| 14. | AG/AG | | | CCC/CYC | ATA/ATR | GGA/GKY | LT/HAZ | 5 | 0 | 0 |
| 15. | AG/AG | | | CCC/CYC | ATG/ATG | | INCONCL | 0 | 4 | 0 |
| 16. | AG/AG | | | CCC/CYC | GYR/ATR | | DK/HAZ | 7 | 0 | 1 |
| 17. | AG/AG | | | CCC/CYC | OTHER | | LT/HAZ | 4 | 0 | 0 |
| 18. | AG/AG | | | CCC/TCC | | | LT/HAZ | 5 | 0 | 0 |
| 19. | AG/AG | | | CCC/CCT | | | HAZ | 4 | 0 | 0 |
| 20. | AG/AG | | | OTHER | | | NOT OBS | 0 | 0 | 0 |
| | | | | | | | TOTAL | 28 | 4 | 1 |
| 21. | CG/CG | CAC/YRC | | CCC/CCC | | | DK/HAZ | 13 | 0 | 0 |
| 22. | CG/CG | CAC/YRC | | CCC/CTC | | | LT/HAZ | 4 | 0 | 0 |
| 23. | CG/CG | CAC/YRC | | OTHER | | | DK | 3 | 0 | 0 |
| 24. | CG/CG | OTHER | | | | | DK | 3 | 0 | 0 |
| | | | | | | | TOTAL | 23 | 0 | 0 |
| 25. | CG/AG | | ATA/ATG | | | | LT/HAZ | 20 | 0 | 2 |
| 26. | CG/AG | | ATG/GCG | | | | LT | 4 | 0 | 0 |
| 27. | CG/AG | | ATA/ATA | CCC/CCC | | | LT/HAZ | 6 | 0 | 1 |
| 28. | CG/AG | | ATA/ATA | OTHER | | | DK/HAZ | 5 | 0 | 0 |
| 29. | CG/AG | | ATG/ATG | | | | INCONCL | 0 | 6 | 0 |
| 30. | CG/AG | | GTA/ATA | | | | DK | 2 | 0 | 0 |
| 31. | CG/AG | | GCG/GCG | | | | DK/HAZ | 2 | 0 | 0 |
| 32. | CG/AG | | GCA/GCA | CCC/CCC | | | LT | 3 | 0 | 0 |
| 33. | | | GCA/GCA | OTHER | | | DK | 1 | 0 | 0 |

TABLE K-continued

Classification tree for using compound genotypes, or compound genotype classes, to categorize individuals as dark or light eye individuals. Similarity with the Tables F, H and H' can be seen, and the root for the claimed methods are based in the empirical observation of trait class counts for various genotypes and genotype combinations.

| TYR2LOC920 | OCA3LOC920 | OCA3LOC109 | MCR3LOC105 | OCA3LOC109 | TYRP3L106 | CLASS | CORR | INCLASS | INCORR |
|---|---|---|---|---|---|---|---|---|---|
| | CG/AG | | | | | | | | |
| 34. | CG/AG | GCA/ATA | CCC/CCC | | | DK | 4 | 0 | 0 |
| 35. | CG/AG | GCA/ATA | CCC/CTC | | | INCONCL | 0 | 3 | 0 |
| 36. | CG/AG | GCA/ATA | CCC/CCT | | | LT | 1 | 0 | 0 |
| 37. | CG/AG | OTHER | | | | NOT OBS | 0 | 0 | 0 |
| | | | | | | TOTAL | 48 | 9 | 3 |
| 38. | CG/CA | ATA/ATA | CCC/YYC | | | LT/HAZ | 15 | 0 | 0 |
| 39. | CG/CA | ATA/ATA | OTHER | | | INCONCL | 0 | 4 | 0 |
| 40. | CG/CA | ATA/ATG | CCC/YYC | | | LT/HAZ | 13 | 0 | 1 |
| 41. | CG/CA | ATA/ATG | CCC/CCT | | | INCONCL | 0 | 4 | 0 |
| 42. | CG/CA | ATA/ATG | OTHER | | | NOT OBS | 0 | 0 | 0 |
| 43. | CG/CA | ATG/ATG | | | | LT/HAZ | 7 | 0 | 0 |
| 44. | CG/CA | ATA/GCA | | | | LT/HAZ | 20 | 0 | 0 |
| 45. | CG/CA | GCA/GCA | | | | INCONCL | 0 | 2 | 0 |
| 46. | CG/CA | ATG/GCG | | | | INCONCL | 0 | 4 | 0 |
| 47. | CG/CA | ATG/ACG | | | | INCONCL | 0 | 1 | 0 |
| 48. | CG/CA | GCA/GCG | | | | DK/HAZ | 4 | 0 | 0 |
| 49. | CG/CA | OTHER | | | | NOT OBS | 0 | 0 | 0 |
| | | | | | | TOTAL | 59 | 15 | 1 |
| ALL CLASSES | | | | | | TOTAL | 211 | 35 | 8 |
| | | | | | | TOTAL* | 96% | | 3% |

In Table K, the elements of the compound genotypes are part of the haplotype systems described herein. Each column represents a unique haplotype system (identified at the top of the table) and each row represents a compound genotype or a compound genotype class (selected as described). The tree is read from left to right along each row. Preceding the first genotype of a row the operator *if* is used. Progressing from column to column requires the operator *and*. The classification for the compound genotype or compound genotype class is shown in column 7: LT—light eyes (blue or green), HAZ—hazel eyes, B1—light brown eyes and DK—dark eyes (black or medium/dark brown). "NOT OBS" signifies that the compound genotype or compound genotype class was not observed. "INCONCL" signifies that no classification could be made because either the sample size was too low or the individuals did not partition among eye color shades in a statistically significant manner (see text). Each deterministic (not INCONCL) classification was justified by a statistically significant chi-square effect statistic (p<0.05). The counts for each compound genotype or compound genotype class are shown in columns 8 (CORR—correctly classified), 9 (IN-CLASS—not classifiable) and 10 (INCORR—incorrectly classified). For example, three (3) dark-eyed and zero (0) light/hazel-eyed individuals were observed for the TYR2LOC920 CG/CG:OCA3LOC920 OTHER (NOT CAC/YRC) (row 24) compound genotype class; this ratio was significantly different from the expected ratio of 3:8 based on the constitution of the study sample. A blank space in a column for a row indicates that the haplotype system for that column was not part of the solution for individuals of that compound genotype or compound genotype class (described in the text). In this case, the solution proceeds to the right until another genotype, or a classification is encountered. The total tabulations are indicated on the last two rows; a "*" indicates that only the classifiable individuals were used for the tabulation (see text). Compound genotypes with low sample sizes that resulted in significant chi-square values were almost always predictive for the darker eye colors which were under-represented in our study sample relative to lighter eye colors.

The roots for the optimal tree selected were genotypes of the TYR2LOC920 haplotype system. The identity and order of the subsequent nodes originating from the various TYR2LOC920 genotype classes were distinct for each particular root. For example, the first node (second haplotype system) selected for TYR2LOC920 AG/CA individuals (rows 1-12, Table K) was the OCA3LOC920 system, though the MCR3LOC105 system was selected as the second node for TYR2LOC920 AG/AG individuals (rows 15-22, Table K). Sometimes classification rules were formulated for compound genotypes (a discrete collection of diploid haplotype pairs from more than one haplotype system), and other times they were formulated for specific compound genotype classes (cognate collections of compound genotypes incorporating elements from a common set of haplotype systems).

The effect statistics for the branching process are shown in Table L below.

compound genotype class can be partitioned into subgroups of distinct genetic structure, the process terminates along a row at the relevant P value for the test, and rules (if any) are derived from the compound genotypes within the class using chi-square statistics (Table L). If they cannot be partitioned in a statistically significant manner, another term is added to the model and the process continues to the next haplotype system on the right. P=INCALC means that the pair-wise FST P value was not calculable. The most common reason for this is genetic homogeneity (only one compound genotype) within one or both of the eye color groups for the compound genotype class which makes the pair-wise method of measurement

TABLE L

Effect statistics for the formulation of classification rules shown in Table K. The effect statistics were decision points used in the generation of Table K.

| | Condition 1 | Condition 2 | Condition 3 | Condition 4 | P VALUE | N |
|---|---|---|---|---|---|---|
| 1) | TYR2LOC920 AG/CA | OCA3LOC920 CAC/CAC | MCR3LOC106 CCC/CYC | TYRP3L105 | P < 0.001 +/− 0.001 | 33 |
| 2) | TYR2LOC920 AG/CA | OCA3LOC920 CAC/CAC | MCR3LOC106 OTHER | | P = 0.027 +/− 0.014 | 15 |
| 3) | TYR2LOC920 AG/CA | OCA3LOC920 YGC/CRC | MCR3LOC106 | | P < 0.001 +/− 0.001 | 14 |
| 4) | TYR2LOC920 AG/AG | MCR3LOC106 CCC/CYC | OCA3LOC109 ATA/ATR | TYRP3L105 | P = 0.045 +/− 0.024 | 8 |
| 5) | TYR2LOC920 AG/AG | MCR3LOC106 CCC/CYC | OCA3LOC109 OTHER | | P = INCALC | 16 |
| 6) | TYR2LOC920 AG/AG | MCR3LOC106 OTHER | | | P = 0.027 +/− 0.014 | 9 |
| 7) | TYR2LOC920 CG/CG | OCA3LOC920 YRC/CAC | MCR3LOC106 | | P < 0.001 +/− 0.001 | 20 |
| 8) | TYR2LOC920 CG/CG | OCA3LOC920 OTHER | | | P = INCALC | 3 |
| 9) | TYR2LOC920 CG/AG | OCA3LOC109 ATA/ATA | MCR3LOC106 | | P = 0.036 +/− 0.020 | 12 |
| 10) | TYR2LOC920 CG/AG | OCA3LOC109 GCA/GCA | MCR3LOC106 | | P = INCALC | 4 |
| 11) | TYR2LOC920 CG/AG | OCA3LOC109 GCA/ATA | MCR3LOC106 | | P = INCALC | 8 |
| 12) | TYR2LOC920 CG/AG | OCA3LOC109 | | | P = 0.045 +/− 0.015 | 58 |
| 13) | TYR2LOC920 CG/CA | OCA3LOC109 ATA/ATA | MCR3LOC106 | | P = INCALC | 19 |
| 14) | TYR2LOC920 CG/CA | OCA3LOC109 ATA/ATG | MCR3LOC106 | | P = INCALC | 18 |
| 15) | TYR2LOC920 CG/CA | OTHER | | | P = 0.018 +− 0.018 | 38 |

In Table L, each row represents a compound genotype class (containing more than one compound genotype), and it is from these classes that the specific compound genotypes or nested genotype classes were obtained for constructing classification rules. The pair-wise F-statistic P values for branching decisions are shown in column 5; they measure the genetic distinction between the light and dark eye groups of individuals within each compound genotype class. The precise rules are derived from these compound genotype classes and justified by significant chi-square effect statistics. Elements of each compound genotype class (its constituent haplotypes or haplotype classes) are indicated column by column Degenerate nucleotide positions are indicated with IUB codes. The tree is read from left to right starting with the operator *if*. The first column contains the root (see text) of a compound genotype class. Progressing to the next column to the right, the operator *and* is used to include the second element of the compound genotype (i.e. the first node), and then the third (if any) and so on until a statistically significant partition can be made within the compound genotype class (if any). If individuals of different eye color shades within a impractical. As with the other cases, significant chi-square effect statistics were used to justify branching to classification leaves (or inconclusive status) for compound genotypes within these compound genotype classes. The sample size for each compound genotype class is shown in the last column.

Comparing this Table L with the specific rules in Table K it is clear that most decisions to formulate classification rules for a compound genotype were justified by the existence of statistically significant population level genetic structure differences within the compound genotype class from which it was derived. A number of rules were formed from compound genotype classes for which measures of population level genetic structure differences were not calculable. Usually, this was because there was only one compound genotype class for one or both of the eye color or eye color shade groups (the test requires genetic diversity within each population). In these cases, the justification for formulating classification rules form the compound genotype classes, or compound genotypes, were justified by significant chi-square effect statistics ($p<0.05$) for genotype distribution of among the eye color shades (at the level of the compound genotype class, considering the distribution of compound genotypes among eye color shades as well as at the level of the compound genotypes themselves).

Sometimes, rules could be constructed for compound genotypes derived from compound genotype classes of small sample size (i.e. n<15) because the distribution of genotypes among the eye color shades were dearly partitioned as measured using the chi-square test. For example, only nine (9) individuals were part of the TYR2LOC920 AG/AG:MCR3LOC106 OTHER (not CCC/CYC) compound genotype class in Table L, but these 9 individuals partitioned nicely among the eye color groups with a F-statistic P=0.027+/−0.014 (row 6, Table L) and each of the chi-square p-value for classifying the two constituents of this compound genotype class (TYR2LOC920 AG/AG:MCR3LOC106 CCC/TCC and TYR2LOC920 AG/AG:MCR3LOC106 CCC/CCF) as light eyed and hazel, respectively, was below 0.05 (rows 18, 19, Table K).

Tabulating the number of correct and incorrect classifications that result from application of the optimal classification tree (Table K), we observed that 211 individuals were correctly classified, whereas only eight (8) were misclassified (i.e. were confounders). Thus, the accuracy rate of the solution was 96.3%. Thirty-three (33) individuals were not classified due to small sample sizes for groups within which they were part. Others were of groups with adequate sample sizes but the chi-square statistics for the compound genotypes (or genotype classes) were insignificant. The haplotype phase of twenty-seven (27) other individuals were not certain at the 75% level, and thus no classification could be made for them. Combining the inconclusive determinations with the un-haplotypable, a total of sixty-two (62) individuals were not classifiable in our study. Thus, the solution exhibited a utility for 81% of Caucasians tested, but within haplotype-certain individuals, the solution exhibited a utility for 86%. The solution was also tested on individuals of other races (Asians and African Americans). When applied to a second group of eye color known Caucasians (n=124), the model generalized well (96% accurate). When applied to African Americans, Caucasians, and Asians, the accuracy of our solution improved to 99.9%, with 98% of the individuals being classifiable.

Final Comments. What has been developed is a novel technique for complex genetics classification that captures all three main components of genetic variance (namely, additivity, dominance, and interaction) in an efficient computational manner. The present technique uses a statistical significance for a gene variant, along with the combinations within which the variant are found, in order to predict a genetic trait. Encodings are given to the presence of specific genotypes and genotype combinations that were identified as significantly associated with the trait from a list of all observed genotypes and genotype combinations, and various discriminate procedures are then used to identify "rules" for making classifications. A classification tree method may be used to identify "rules" from the list for making classifications. The foundation of both methods is the list of observed trait class counts for all observed genotypes and genotype combinations.

Preferably, the methods and apparatus for use in genetic trait classification involve at least two genes associated with a genetic trait. In one illustrative method, a value for use in classifying an individual into one of a plurality of trait classes associated with the genetic trait is calculated. The value is calculated based on (1) a sum of contributions associated with each genotype of a plurality of genotypes of the at least two genes identified for the individual, where the contributions for each genotype are identified at least in part from statistical associations between the genotypes and each trait class identified from a sample population; and (2) a sum of contributions associated with one or more genotype combinations between the at least two genes identified for the individual, where the contributions for the one or more genotype combinations are identified at least in part from statistical associations between the genotype combinations and each trait class identified from the sample population. A genetic trait classification test may include a computer storage medium and computer instructions stored on the computer storage medium for executing such a method on a computer processor.

In another illustrative method, a first statistical association is created between each one of a plurality of genotypes of the at least two genes and counts of individuals of a sample population associated with each one of a plurality of trait classes of the genetic trait. In addition, a second statistical association is created between each one of all genotype combinations of the at least two genes and counts of the individuals of the sample population associated with each one of the plurality of trait classes of the genetic trait. Based on the first and the second statistical associations, one or more mathematical expressions are formulated and provided for classifying an individual outside of the sample population into one of the plurality of trait classes of the genetic trait. For example, a plurality of p-values may be calculated based on the first statistical association and the one or more mathematical expressions may be provided with contributions based on the plurality of calculated p-values. As another example, one or more genotype combinations associated with a trait class having a count percentage in the sample population that exceeds a threshold may be identified from the second statistical association, and the one or more mathematical expressions may be provided with contributions associated with the one or more identified genotype combinations. Also, a genetic trait classification test may include a computer storage medium and computer instructions stored on the computer storage medium for performing such methods.

What is claimed is:

1. A blind genetics classification method in a computing device for use in blind genetic trait classification of an individual sample outside of a sample population involving analysis of at least two genes associated with a genetic trait, the method comprising the acts of:

receiving, in the computing device from the individual sample, each genotype of a plurality of genotypes of the at least two genes found in the individual sample;

receiving, in the computing device from the individual sample, each genotype combination of one or more predetermined genotype combinations of the at least two genes found in the individual sample;

calculating, by the computing device, a value for classifying the individual sample outside of the sample population into one of a plurality of trait classes associated with the genetic trait based on a summation of:

a first sum of contributions associated with each said genotype of the plurality of genotypes of the at least two genes in the individual sample, the contribution for each said genotype being a function of a calculated statistical value for the genotype determined from coupts of individuals in the sample population associated with each trait class of the genetic trait, the calculated statistical value comprising a p-value and the first sum of contributions being representable by the mathematical expression "$\Sigma n v_i$" for all genotypes i, where $v_i = \log (c/p_i)$, $p_i$ is the p-value, c is a constant greater than or equal to 0.05, and n is a variable for each different trait class, and a second sum of contributions associated with each said genotype combination of the one or more predetermined genotype combinations in the individual sample, each said one or more predetermined genotype combination being selected from the sample population based on having a statistically significant association with one of the trait classes of the genetic trait;

classifying the individual sample outside of the sample population into one of the plurality of trait classes of the genetic trait based on the calculated value, and providing a classification result corresponding to the classified individual sample; and providing the classification result to an output device for observation.

2. The method of claim 1, wherein each statistically significant genotype combination has a count percentage in the sample population which exceeds a threshold.

3. The method of claim 1, wherein each statistically significant genotype combination has a count percentage in the sample population over 94%.

4. The method of claim 1, wherein the act of classifying the individual into one of the plurality of trait classes is performed based on selecting threshold values for the trait classes.

5. The method of claim 1, wherein the first and the second sum of contributions takes additive, dominance, and epistatic components into account for the genetic trait classification.

6. The method of claim 1, wherein the second sum of contributions may be represented by the mathematical expression $$\Sigma nc_j$$

for all significant genotype combinations j, where $c_j=0$ if the jth genotype combination is not present in the individual and $c_j=1$ if the jth genotype combination is present in the individual, and n is a variable for each different trait class.

7. The method of claim 1, wherein the summation is representable by the mathematical expression $$\Sigma nv_i + \Sigma nc_j$$

for all genotypes i and for all significant genotype combinations j, where $\Sigma nc_j$ is the second sum of contributions where $c_j=0$ if the jth genotype combination is not present in the individual and $c_j=1$ if the jth genotype combination is present in the individual, and n is a variable for each different trait class.

8. The method of claim 1, wherein the genetic trait comprises eye color.

9. The method of claim 1, wherein the genetic trait comprises a response to a particular drug.

10. The method of claim 1, wherein the genetic trait comprises a particular disease.

11. The method of claim 1, wherein the acts of the method are performed by computer program instructions in a computer readable medium utilized by the computing device.

12. A blind classification test process for a computing device for producing a genetic trait class identification for an individual sample outside of a sample population, the genetic trait class identification corresponding to one of a plurality of trait classes of a genetic trait, the blind classification test process being adapted for receiving, in the computing device from the individual sample, each genotype of a plurality of genotypes of at least two genes found in the individual sample; receiving, in the computing device from the individual sample, each genotype combination of one or more predetermined genotype combinations of the at least two genes found in the individual sample; calculating by the computing device a value from a summation of (1) a first sum of contributions associated with each said genotype of the plurality of genotypes of the at least two genes in the individual sample, wherein the contribution for each said genotype is a function of a calculated statistical value for the genotype determined from counts of individuals in the sample population associated with each trait class of the genetic trait, the calculated statistical value comprising a p-value and the first sum of contributions being representable by the mathematical expression "$\Sigma nv_i$" for all genotypes i, where $v_i = \log(c/p_i)$, $p_i$ is the p-value, c is a constant greater than or equal to 0.05, and n is a variable for each different trait class, and (2) a second sum of contributions associated with each said genotype combination of the one or more predetermined genotype combinations in the individual sample, wherein each said one or more predetermined genotype combination is identified from the sample population based on having a statistically significant association with one of the trait classes of the genetic trait; producing the genetic trait class identification for the individual based on the calculated value; and providing the genetic trait class identification at an output device for observation.

13. The blind classification test process of claim 12, wherein the second sum of contributions being representable by the mathematical expression "$\Sigma nc_j$" for all significant genotype combinations j, where $c_j=0$ if the jth genotype combination is not present in the individual and $c_j=1$ if the jth genotype combination is present in the individual, and n is a variable for each different trait class.

14. The blind classification test process of claim 12, wherein each statistically significant genotype combination has a count percentage in the sample population which exceeds a threshold.

15. A blind genetics classification method for use in blind genetics classification involving at least two genes associated with a genetic trait, the method comprising the acts of:

creating associations between one or more statistically significant genotype combinations of the at least two genes and counts of individuals of a sample population that fall into each one of a plurality of trait classes of the genetic trait;

creating a mathematical expression for classifying an individual sample outside of the sample population into one of the plurality of trait classes of the genetic trait based on the created associations, the mathematical expression being based in part on $$\Sigma nc_j$$

for all significant genotype combinations j, where $c_j=0$ if the jth genotype combination is not present in the individual and $c_j=1$ if the jth genotype combination is present in the individual, and n is a variable for each different trait class;

providing the mathematical expression in a classification test process operative in a computing device; and providing the classification test process for classifying the individual sample outside of the sample population into one of the plurality of trait classes of the genetic trait, the classification test process being operative in the computing device for receiving, in the computing device from the individual sample, each genotype combination of the one or more statistically significant genotype combinations of the at least two genes found in the individual sample; calculating by the computing device a value from the mathematical expression which depends on which genotype combinations of the at least two genes are found in the individual sample; producing a classification result based on the calculated value for classifying the individual sample into one of the plurality of trait classes of the genetic trait; and providing the classification result at an output device for observation.

16. The method of claim 15, wherein each statistically significant genotype combination has a count percentage in the sample population which exceeds a threshold.

17. A blind genetics classification method in a computing device for use in blind genetic trait classification of an individual sample outside of a sample population involving analysis of at least two genes associated with a genetic trait, the method comprising the acts of:

receiving, in the computing device from the individual sample, each genotype of a plurality of genotypes of the at least two genes of the individual sample;

receiving, in the computing device from the individual sample, each genotype combination of one or more predetermined genotype combinations of the at least two genes of the individual sample;

calculating, by the computing device, a value for classifying the individual sample outside of the sample population into one of a plurality of trait classes associated with the genetic trait based on a summation of:

a first sum of contributions associated with each said genotype of the plurality of genotypes of the at least two genes in the individual sample, the contribution for each said genotype being a function of a calculated statistical value for the genotype determined from counts of individuals in the sample population associated with each trait class of the genetic trait, the calculated statistical value comprising a p-value, a second sum of contributions associated with each said genotype combination of the one or more predetermined genotype combinations in the individual sample, each said one or more predetermined genotype combination being selected from the sample population based on having a statistically significant association with one of the trait classes of the genetic trait; and providing the calculated value to an output device for observation; and wherein the summation is representable by the mathematical expression $$\Sigma nv_i + \Sigma nc_j$$

for all genotypes i and for all significant genotype combinations j, where $\Sigma nv_i$ is the first sum of contributions where $v_i = \log(c/p_i)$, $p_i$ is the p-value, c is a constant greater than or equal to 0.05, and n is a variable for each different trait class, and where $\Sigma nc_j$ is the second sum of contributions where $c_j = 0$ if the jth genotype combination is not present in the individual and $c_j = 1$ if the jth genotype combination is present in the individual, and n is a variable for each different trait class.

* * * * *